US00PP14254P29

(12) United States Plant Patent
Anderson

(10) Patent No.: US PP14,254 P2
(45) Date of Patent: Oct. 28, 2003

(54) DAHLIA PLANT NAMED 'BALNOVCHES'

(50) Latin Name: *Dahlia pinnata*
Varietal Denomination: Balnovches

(75) Inventor: Neil Anderson, St. Paul, MN (US)

(73) Assignee: Ball FloraPlant, a division of Ball Horticultural Company, West Chicago, IL (US)

( * ) Notice: Subject to any disclaimer, the term of this patent is extended or adjusted under 35 U.S.C. 154(b) by 0 days.

(21) Appl. No.: 10/109,507

(22) Filed: Mar. 27, 2002

(51) Int. Cl.[7] ..... A01H 5/00
(52) U.S. Cl. ..... Plt./321
(58) Field of Search ..... Plt./321

*Primary Examiner*—Kent Bell
(74) *Attorney, Agent, or Firm*—Wood, Phillips, Katz, Clark & Mortimer

(57) ABSTRACT

A new and distinct Dahlia plant named 'Balnovches', characterized by its yellow inflorescences with red accents, upright mounded form and moderately vigorous growth habit, is provided.

1 Drawing Sheet

Latin name of genus and species of plant claimed: *Dahlia pinnata.*
Variety denomination: 'Balnovches'.

BACKGROUND OF THE INVENTION

The present invention comprises a new and distinct Dahlia plant, botanically known as *Dahlia pinnata* and hereinafter referred to by the cultivar name 'Balnovches'.

The new cultivar is the product of a planned breeding program. The female (seed) parent of 'Balnovches' was the *Dahlia pinnata* variety 'Figaro White' (unpatented) which exhibits white inflorescences. The male (pollen) parent of 'Balnovches' was a mix of pollen from the *Dahlia pinnata* series 'Figaro Improved' (unpatented), which may exhibit inflorescences of red, rose, mauve, salmon, yellow or white. The new Dahlia was discovered and selected as a single flowering plant from within the progency of the above stated cross during 1998–1999 in Elburn, Ill. and was initially designated 'PAS11428-3'.

Asexual reproduction of the new cultivar by terminal tip cuttings taken during 2001 at West Chicago, Ill., has demonstrated that the characteristics of the new cultivar as herein described are firmly fixed and are retained through successive generations of such asexual propagation.

SUMMARY OF THE INVENTION

It was found that the cultivar of the present invention:

(a) exhibits upright mounded form;

(b) forms semi-double yellow inflorescences with red accents; and (c) exhibits a moderately vigorous growth habit.

'Balnovches' has not been observed under all possible environmental conditions to date. Accordingly, it is possible that the phenotype may vary somewhat with variations in the environment, such as temperature, light intensity, and day length.

The new cultivar of the present invention can be compared to 'Linda' (U.S. Plant Pat. No. 7,779). However, in side-by-side comparisons, 'Balnovches' exhibits ray florets of a different color and fewer ray florets per inflorescence than 'Linda'.

BRIEF DESCRIPTION OF PHOTOGRAPH

The accompanying photograph shows as nearly true as it is reasonably possible to make the same in color illustrations of this type, typical flower and foliage characteristics of the new cultivar. The plants were grown for nine (9) weeks in a greenhouse at West Chicago, Ill.

DETAILED BOTANICAL DESCRIPTION

The chart used in the identification of colors described herein is The R.H.S Colour Chart of The Royal Horticultural Society, London, England. The color values were determined on Nov. 21, 2001 in West Chicago, Ill. The readings were taken between 10:00 and 11:45 a.m. under natural light conditions. The plants were produced from cuttings taken from stock plants and were grown in 15 cm pots in a double polycarbonate covered greenhouse under conditions comparable to those used in commercial practice. The plants were grown while utilizing a soilless growth medium and maintaining temperatures of approximately 65° to 70° F. (18° to 21° C.) during the day and approximately 60° to 65° F. (15° to 18° C.) during the night. Light levels between 4,000 and 6,000 footcandles were maintained. Plants were nine (9) weeks after the planting of rooted cuttings.

Classification:
- *Botanical.*—*Dahlia pinnata* cultivar 'Balnovches'.
- *Commercial.*—Dahlia.

Parentage:
- *Female parent.*—'Figaro White'.
- *Male parent.*—Mix of pollen from plants of the 'Figaro Improved' series.

Propagation:
- *Type cutting.*—Terminal tip.
- *Time to initiate roots.*—Approximately 10 to 14 days.
- *Time to develop roots.*—Approximately 21 to 28 days.
- *Root description.*—Fibrous and well branched.
- *Tubers.*—Will form under short day conditions of at least 13 to 14 hours of darkness.

Plant description:
- *General appearance and form.*—Upright and mounded.

*Height above pot.*—Foliage only: approximately 9 cm. Whole plant: Approximately 17 cm.

*Width.*—Approximately 21.8 cm.

*Branching habit.*—Freely branching. Pinching 14 to 21 days after transplanting helps to improve basal branching.

*Branch description.*—Length: Approximately 7.2 cm. Diameter: Approximately 4 mm. Color: 146B. Texture: Smooth. Internode length: Approximately 1.6 cm.

Foliage description:

*Form.*—Mature foliage is simple, occasionally trifoliate.

*Shape.*—Ovate.

*Margin.*—Dentate.

*Apex.*—Acute.

*Base.*—Attenuate.

*Arrangement.*—Opposite.

*Surface.*—Upper and lower surfaces are dull and the upper surface is slightly rugose.

*Color of mature foliage.*—Upper surface: Closest to 137A with veins of 145A.

*Color of mature foliage.*—Lower surface: Closest to 191A with veins of 145A.

*Size.*—Size — Single mature leaf is approximately 5.2 cm in length and approximately 3.5 cm in width. Mature compound (trifoliate) leaves are approximately 6 cm in length and 5.3 cm in width. Terminal leaflet is approximately 5.5 cm in length and 3.5 cm in width. Lateral leaflets are approximately 3.7 cm in length and approximately 1.8 cm in width. Petiole is 2.5 cm in length, 3 mm in diameter and 145A in color. Individual leaflets are sessile.

Flower description:

*Outdoor flowering habit.*—'Balnovches' is freely flowering under outdoor growing conditions with substantially continuous blooming from spring through fall.

*Appearance.*—Semi-double, arising from leaf axils on strong peduncles. Disc and ray florets arranged acropetally on a capitulum.

*Flower bud.*—Shape: Round. Length: Approximately 1.4 cm. Diameter: Approximately 1.2 cm. Color: Darker than 71A.

*Inflorescence.*—Diameter: Approximately 7.9 cm. Depth: Approximately 2.3 cm. Disc diameter: Approximately 2.2 cm. Number per Plant: Approximately 4.

*Ray florets.*—Quantity: Approximately 16.4 per inflorescence. Shape: Elongated, cupped. Length: Approximately 3.6 cm. Apex: Pointed to slightly rounded. Base: Attenuate. Margin: Entire. Texture: Smooth. Color: Fully opened, upper surface of outer whorl is 185D at tip, 179D in the center and 2A at the base. Fully opened, lower surface of outer whorl is 186B with 3A at base. Fully opened upper surface inner whorls is 59C at tip, 179D in center and 3A at base. Fully opened lower surface of inner whorls is 59A at tip 179D in center and 3A at base. Ray floret color fades to 187C with age.

*Disc florets.*—Number per inflorescence: Approximately 51. Shape: Elongated, cylindrical. Length: Approximately 1.3 cm. Diameter: Approximately 3 mm. Color: 7A, transparent.

*Peduncle.*—Strong, erect. Length: Approximately 7 cm. Diameter: Approximately 2 mm. Texture: Smooth. Color: 146C.

*Involucral bracts.*—Quantity: 8. Shape: Diamond-shaped. Tip: Broadly acute. Margin: Entire. Texture: Smooth. Color: Upper and lower surface is 137C with venation of 137A. Bract length: Approximately 1.4 cm. Bract width: Approximately 6 mm.

*Reproductive organs.*—Androecium — On disc florets. Anthers are feather shaped and approximately 3 mm in length. Anther color: 14A. Pollen is 24A and abundant. Gynoecium — On disc and ray florets. Pistil number per disc floret: One (1). Pistil length: Approximately 7.5 mm. Stigma length: 2.5 mm. Stigma color: 150C. Style length: 2.5 mm. Style color: 145D. Ovary length: 2.5 mm. Ovary color: 145B. Lastingness of individual bloom is approximately ten (10) days.

Seed production: Seed production has not been observed.

Disease resistance: Disease resistance has not been observed.

Weather tolerance: The weather tolerance of the new Dahlia has been shown to be typical for Dahlias.

I claim:

1. A new and distinct Dahlia plant named 'Balnovches' substantially as herein shown and described, which:

(a) exhibits an upright mounded form;

(b) forms semi-double yellow inflorescences with red accents; and (c) exhibits a medium vigorous growth habit.

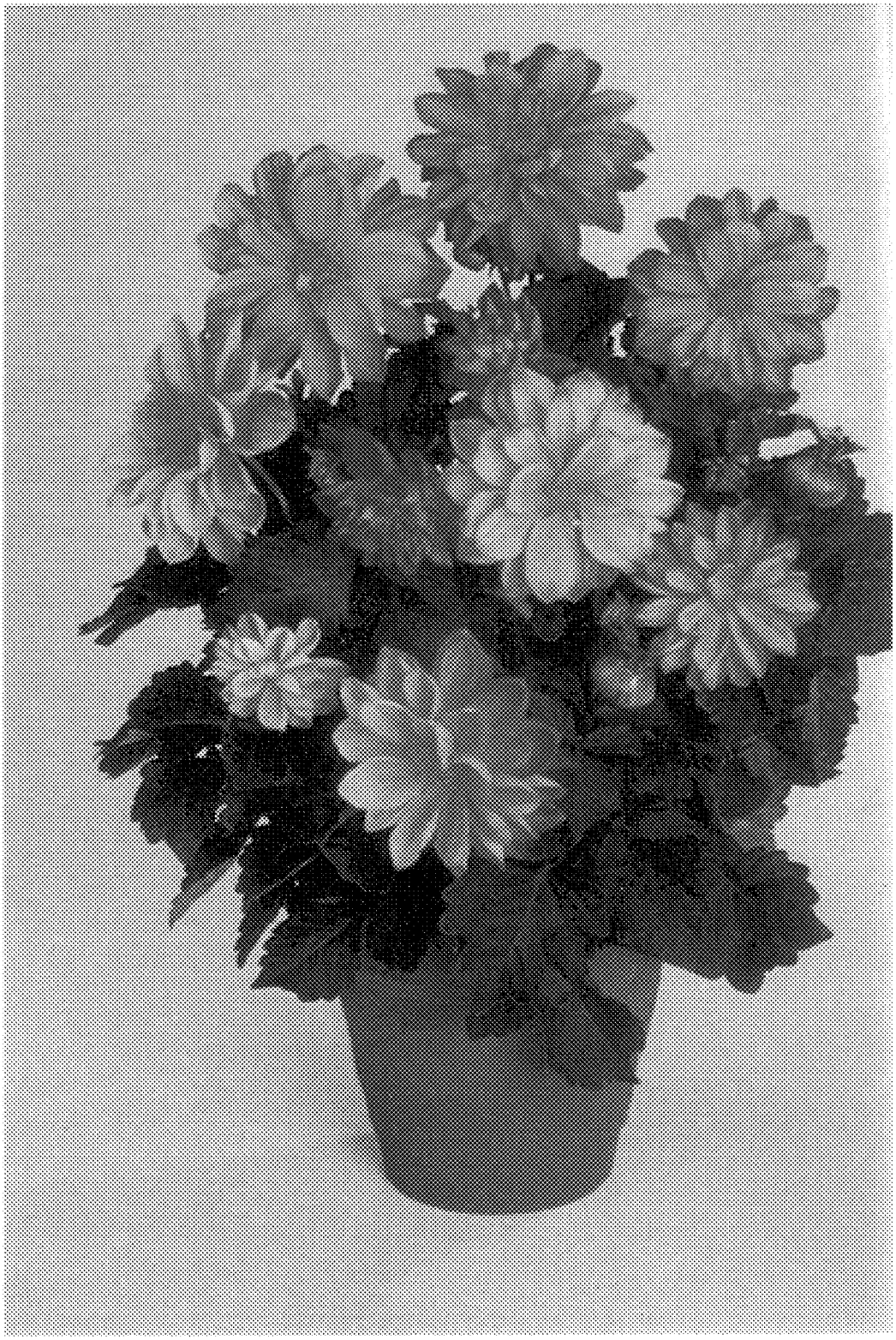

* * * * *